(12) United States Patent
Deshmukh

(10) Patent No.: US 7,442,707 B2
(45) Date of Patent: Oct. 28, 2008

(54) CCI-779 POLYMORPH AND USE THEREOF

(75) Inventor: Subodh S. Deshmukh, White Plains, NY (US)

(73) Assignee: Wyeth, Madison, NJ (US)

( * ) Notice: Subject to any disclaimer, the term of this patent is extended or adjusted under 35 U.S.C. 154(b) by 236 days.

(21) Appl. No.: 11/339,728

(22) Filed: Jan. 25, 2006

(65) Prior Publication Data

US 2006/0178392 A1 Aug. 10, 2006

Related U.S. Application Data

(60) Provisional application No. 60/651,374, filed on Feb. 9, 2005.

(51) Int. Cl.
*C07D 498/18* (2006.01)
*A61K 31/395* (2006.01)

(52) U.S. Cl. ...................... 514/291; 540/456

(58) Field of Classification Search ................. 540/456; 514/291
See application file for complete search history.

(56) References Cited

U.S. PATENT DOCUMENTS

| 5,362,718 | A | 11/1994 | Skotnicki et al. |
| 6,277,983 | B1 | 8/2001 | Shaw et al. |
| 6,677,357 | B2 | 1/2004 | Zhu et al. |
| 6,680,330 | B2 | 1/2004 | Zhu et al. |
| 2005/0014777 | A1 | 1/2005 | Zhu et al. |
| 2005/0033046 | A1 | 2/2005 | Chew et al. |
| 2005/0049271 | A1 | 3/2005 | Benjamin et al. |
| 2005/0234234 | A1 | 10/2005 | Gu et al. |

FOREIGN PATENT DOCUMENTS

| EP | 1 216 251 B1 | 2/2003 |
| EP | 0 763 039 B1 | 3/2003 |
| EP | 1 419 154 B1 | 10/2005 |
| WO | WO 95/28406 A1 | 10/1995 |
| WO | WO 01/23395 A2 | 4/2001 |
| WO | WO 03/018573 A1 | 3/2003 |
| WO | WO 03/018574 A1 | 3/2003 |
| WO | WO 2005/010010 A1 | 2/2005 |
| WO | WO 2005/016935 A2 | 2/2005 |
| WO | WO 2005/023254 A1 | 3/2005 |
| WO | WO 2005/105811 A1 | 11/2005 |

OTHER PUBLICATIONS

Communication- International Search Report in International Application No. PCT/US2006/003098, mailed Jun. 27, 2006.

*Primary Examiner*—Bruck Kifle
(74) *Attorney, Agent, or Firm*—Arnold S. Milowsky; Howson & Howson LLP

(57) ABSTRACT

The present invention provides CCI-779 polymorph Form II. This invention also provides processes for preparing CCI-779 polymorph Form II and pharmaceutical compositions including CCI-779 polymorph Form II.

11 Claims, 5 Drawing Sheets

CCI-779 POLYMORPH AND USE THEREOF

CROSS-REFERENCE TO RELATED APPLICATION

This application claims the benefit under 35 USC 119(e) of U.S. provisional patent application No. 60/651,374, filed Feb. 9, 2005.

BACKGROUND OF THE INVENTION

This invention relates to a CCI-779 polymorph, processes for its preparation and pharmaceutical compositions and kits containing said polymorph.

Rapamycin 42-ester with 3-hydroxy-2-(hydroxymethyl)-2-methylpropionic acid (CCI-779) is an ester of rapamycin. Rapamycin, also termed sirolimus, is a macrocyclic triene antibiotic produced by *Streptomyces hygroscopicus*. The preparation and use of hydroxyesters of rapamycin, including CCI-779, are described in U.S. Pat. Nos. 5,362,718 and 6,277,983.

CCI-779 has been described as having in vitro and in vivo activity against a number of tumor cell types. It is hypothesized that CCI-779 delays the time to progression of tumors or time to tumor recurrence. This mechanism of action is more typical of cytostatic rather than cytotoxic agents and is similar to that of sirolimus.

CCI-779 binds to and forms a complex with the cytoplasmic protein FKBP, which inhibits an enzyme, mTOR (mammalian target of rapamycin, also known as FKBP12-rapamycin associated protein (FRAP)). Inhibition of mTOR's kinase activity inhibits a variety of signal transduction pathways, including cytokine-stimulated cell proliferation, translation of mRNAs for several key proteins that regulate the G1 phase of the cell cycle, and IL-2-induced transcription, leading to inhibition of progression of the cell cycle from G1 to S.

The preparation and use of hydroxyesters of rapamycin, including CCI-779, are described in U.S. Pat. Nos. 5,362,718 and 6,277,983.

SUMMARY OF THE INVENTION

In one aspect, the present invention provides CCI-779 polymorph Form II.

In another aspect, the present invention provides a process for preparing CCI-779 polymorph Form II.

In a further aspect, the present invention provides pharmaceutical compositions containing CCI-779 polymorph Form II.

In yet another aspect, the present invention provides kits containing CCI-779 polymorph Form II.

In still a further aspect, the present invention provides methods of preparing pharmaceutical compositions containing CCI-779 polymorph Form II.

Other aspects and advantages of the present invention are described further in the following detailed description of the preferred embodiments thereof.

BRIEF DESCRIPTION OF THE DRAWINGS

FIG. 3A is the Form II sample obtained from a t-BME slurry. FIG. 3B is the Form II sample obtained from a t-BME/n-heptane slurry. These figures show a broad melting event with a characteristic onset temperature of 105-115° C., which is easily distinguished from the DSC profile for Form I. DSC data was collected using a Q1000 DSC (TA instruments). The sample was heated under a nitrogen flow from 25-200° C. at a ramp rate of 10° C./min.

DETAILED DESCRIPTION OF THE INVENTION

Figure 1:
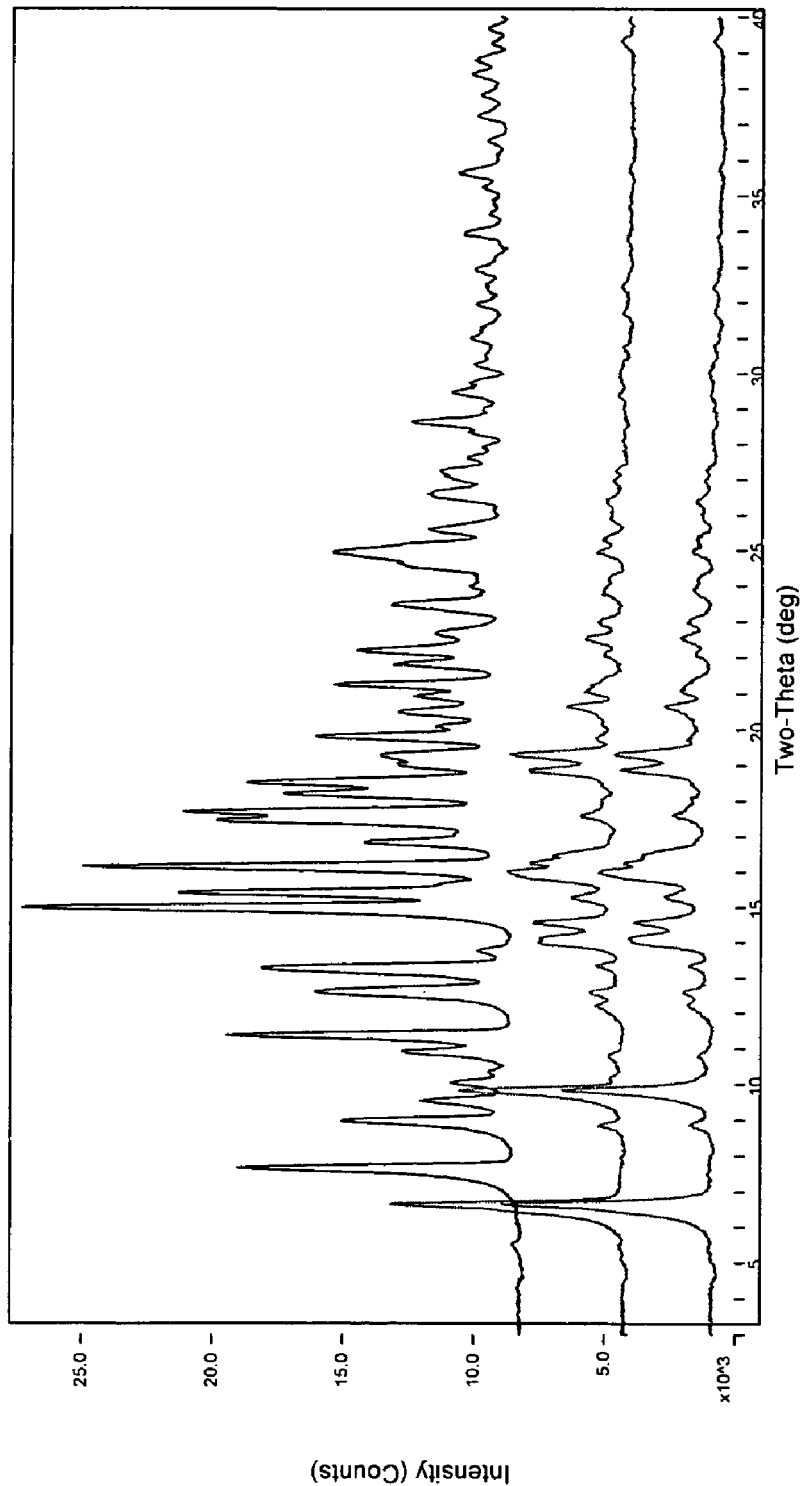
FIG. 1 is a powder X-ray diffraction (XRD) pattern of CCI-779 Form I (the top set of peaks) and Form II (the bottom two sets of peaks). The powder XRD diffraction patterns were obtained on a Rigaku Miniflex Diffraction System (Rigaku MSC Inc.). The powder samples were deposited on a zero-background polished silicon sample holder. A normal focus copper x-ray tube at 0.45 kW equipped with a Ni Kβ filter scanning at 0.25°/minute from 3.00 to 40.00E 2θ was used as the x-ray source. The data processing was done using Jade 6.0 software.

The present invention provides CCI-779 polymorph Form II. CCI-779 polymorph Form II was isolated and characterized by X-ray diffraction (XRD), differential scanning calorimetry (DSC), and thermogravimetric analysis (TGA).

It has been observed from the morphology for CCI-779 Form II (plate-like) at bench scale, that CCI-779 has better powder flow characteristics than form I (needle-like). In other preliminary data, some evidence has shown that Form II is thermodynamically more stable than Form I.

1. Definitions

As used herein, the term "CCI-779" or "CCI-779 Form I" refers to the CCI-779 form currently available to those in the art, which is identified by characteristic and readily available or obtainable high performance liquid chromatography (HPLC) retention times, X-ray crystal structure, powder XRD pattern, and DSC thermogram. The powder XRD pattern of CCI-779 is readily available to those of skill in the art and contains several characteristic peaks of varying intensity at 2θ of about 7.6°, 9.5°, 11.4°, 15.0°, 16.8°, 18.2°, 18.5°, and 21.2°. The differential scanning calorimetry (DSC) thermogram is characterized by a single melt endotherm with onset temperature of 160-166° C.

As used herein, the term "polymorph" refers to a compound (e.g., CCI-779) which, when present as a solid, exists as different forms. Desirably, the CCI-779 polymorph includes solid forms of a compound such as crystals, microcrystals, foams, and powders, among others. Preferably, the CCI-779 polymorphs of the present invention are crystalline. Polymorphs typically differ in their physical properties due to the order of the molecules in the lattice of the polymorph. In addition, the physical properties of the polymorph can differ due to the presence of solvates or other molecules incorporated into the lattice of the polymorph. Typically, polymorphs are readily distinguished using techniques such as melting point, rate of dissolution, Infrared (IR) and Raman spectroscopy, and X-ray diffraction such as crystal and powder techniques.

The term "amorphous" as used herein refers to a compound having no definite crystal structure or form. In the present application, the term amorphous refers to amorphous CCI-779 that can be present in the amorphous form as a solid or in a solution.

The term "precipitation" or "precipitating" is meant to describe a process by which a solid form of a compound is precipitated from a solution containing dissolved compound. As used herein, precipitation is meant to describe precipitating CCI-779 polymorph Form II from a solution of CCI-779, preferably in t-butyl methyl ether.

Accordingly this invention provides a process for preparing CCI-779 polymorph Form II, comprising the steps of:
  (a) dissolving CCI-779 in an initial solvent, eg acetone;
  (b) removing said initial solvent in step (a) to form a solid foam;
  (c) mixing the solid foam with t-butyl methyl ether (t-BME); and
  (d) collecting said CCI-779 polymorph Form II.
  In step c) t-BME may be added in an amount sufficient to form a solid suspension. The suspension may be washed with t-BME and dried under vacuum to obtain dry crystalline Form II solid.

The mixture of solid foam with t-BME resulting from step c) may be mixed with n-heptane to form a solid suspension. In a further step the solid is collected, washed with n-heptane, and dried under vacuum to obtain dry crystalline Form II solid.

The term "room temperature" is meant to describe a temperature of about 23 to about 25° C. However, one of skill in the art would readily understand that the specific room temperature can vary depending upon the conditions utilized during the formation of CCI-779 polymorph Form II and environmental conditions.

II. Characterization of CCI-779 Polymorph Form II

Characterization of CCI-779 polymorph Form II and distinguishing the same from CCI-779 is accomplished using techniques known to those of skill in the art. Specifically, verification that CCI-779 polymorph Form II is present after precipitation can be performed using techniques including melting point, infrared spectroscopy (IR), nuclear magnetic resonance spectroscopy (NMR), mass spectral analysis (MS), combustion analysis, Raman spectroscopy, elemental analysis, and chromatography including high performance liquid chromatography (HPLC). Other techniques including differential scanning calorimetry (DSC) and X-ray diffraction (XRD) are also useful in distinguishing polymorphs, and specifically, CCI-779 polymorph Form I from CCI-779 polymorph Form II.

(A) Identification Using Spectroscopy

HPLC can be utilized to verify that the product obtained as noted above is CCI-779 polymorph Form II. Preferably, the CCI-779 Form II polymorph is analyzed using HPLC-Ultra Violet (UV) or HPLC-Mass Spectral (MS) spectroscopy using the techniques described in French et al., Clinical Chemistry, 47(7): 1316 (2001) and Holt et al., Clinical Chemistry, 46(8): 1179 (2000), which are hereby incorporated by reference.

Desirably, the HPLC chromatograph of CCI-779 polymorph Form II is identical to the HPLC chromatograph of CCI-779 using the conditions described in French and Holt noted above. The HPLC chromatograph of CCI-779 polymorph Form II may contain additional peaks that correspond to impurities that can be readily identified by one of skill in the art. However, one of skill in the art would readily understand that the presence of the impurities does not interfere with identification and characterization of CCI-779 polymorph Form II.

A variety of HPLC conditions useful for obtaining a HPLC chromatograph can readily be determined by one of skill in the art, and should not be considered a limitation on the present invention. These HPLC conditions include variations in the column temperature, flow rate, detection wavelength, column type, column size, and mobile phase, among others. In one embodiment, the HPLC-MS conditions include the conditions set forth in Holt noted above. For example, the conditions include a 15 centimeter (cm)×4.6 mm Supelcosil™ LC-18-DB column containing 5 micron (μ) ODS particles, a temperature of about 50° C., and a flow rate of about 1.0 milliliter (mL)/minute. A variety of mobile phases can be utilized to obtain an HPLC-UV chromatograph of CCI-779 polymorph Form II. In one embodiment, the mobile phase is a methanol:water (for example, 80:20 by volume) solution optionally supplemented with an ammonium acetate solution or other solvent such as acetonitrile and/or dioxane, among others.

By using the HPLC-MS conditions as noted above, the HPLC chromatograph for CCI-779 polymorph Form II has a retention time identical to that of CCI-779 polymorph Form I. The HPLC-MS chromatograph of CCI-779 polymorph Form II can then be compared to the HPLC-MS of CCI-779 using the same HPLC-MS conditions. In the present invention, the retention time for CCI-779 polymorph Form II should be identical to the retention time for CCI-779 Form I.

Typically, XRD and DSC techniques are utilized as further confirmation to verify that CCI-779 polymorph Form II is present.

(B) Identification Using X-ray Diffraction

XRD techniques are utilized to distinguish CCI-779 polymorph Form II from CCI-779. One of skill in the art would readily be able to determine the conditions required to obtain an XRD pattern of CCI-779 polymorph Form II. A variety of XRD instruments are available and include the Scintag™ X-2 Advanced Diffraction System instrument using the Diffraction Management Software NT program, among others.

The powder XRD pattern of CCI-779 polymorph Form II described herein was therefore obtained using X-ray crystallographic techniques known to those of skill in the art. In one embodiment, the XRD pattern of CCI-779 polymorph Form II includes multiple peaks that differ from the XRD peaks obtained for CCI-779 Form I. In another embodiment, the XRD pattern of CCI-779 polymorph Form II contains one large peak and several smaller peaks. In a further embodiment, the XRD pattern of CCI-779 polymorph Form II contains representative peaks at 2θ of about 6.6°, 9.8°, 14.0°, 14.1°, 14.5°, and 18.8°.

Other peaks can also be present in the XRD pattern of CCI-779 polymorph Form II and correspond to impurities in the sample. The other peaks typically correspond to minor amounts of CCI-779 and/or free t-butyl methyl ether not incorporated into the matrix of CCI-779 polymorph Form II.

In addition to characterizing CCI-779 polymorph Form II, XRD can be used to monitor the formation of CCI-779 polymorph Form II. Typically, samples are obtained at various stages during dissolution in the dissolving solvent and during precipitation of CCI-779 polymorph Form II for example, as a slurry in the solvent system used, as a solvent-wet cake, as a partially dried (under air or nitrogen gas) solid and as a dry solid as determined by constant weight and the XRD patterns obtained therefrom.

(C) Identification Using Differential Scanning Calorimetry

Differential scanning calorimetry (DSC) techniques can also be utilized to distinguish CCI-779 polymorph Form II from CCI-779. One of skill in the art would readily be able to determine the conditions necessary to obtain a DSC thermogram of CCI-779 polymorph Form II. A variety of differential scanning calorimeters are available by those of skill in the art and include the Pyris™ 1 DSC instrument, using temperatures of about 25° C. to about 220° C. and temperature increases at various rates including 5° C./min., 10° C./min., and 30° C./min., among other instruments and conditions.

The DSC thermogram of CCI-779 polymorph Form II prepared according to the present invention contains an endotherm with an onset temperature of about 105° C., which is not present in the DSC thermogram for the Form I polymorph. See, FIG. 2. The DSC thermogram of CCI-779 polymorph Form II can also include degradation endotherms.

(D) Identification Using Thermogravimetric Analysis (TGA)

TGA can also be utilized to determine the presence of solvate molecules, such as t-BME molecules, in the sample of CCI-779 polymorph Form II. In the present invention, TGA data for the Form II polymorph shows a gradual weight less of less 1 wt % on heating from 25° C. to 150° C. One of skill in the art would readily be able to determine the instruments and conditions utilized during TGA.

III. Compositions Containing CCI-779 Polymorph Form II

Compositions containing CCI-779 polymorph Form II can also be prepared according to the present invention. Such compositions are prepared by combining CCI-779 polymorph Form II and a pharmaceutically acceptable carrier.

In one embodiment, the invention provides a composition or mixture of CCI-779 polymorph Form II along with one or more other crystalline, polymorphic, solvate, amorphous, or other forms of CCI-779. For example, such a composition may comprise CCI-779 polymorph Form II along with one or more other forms of CCI-779, such CCI-779 and/or CCI-779 polymorph Form I. For example, the composition may comprise less than 1%, 2%, 5%, 10%, 20%, 30%, 40% or 50% by weight of CCI-779 polymorph Form II or CCI-779 polymorph Form I based on the total amount of the composition.

Prior to administration, and in further embodiment, CCI-779 polymorph Form II may be formulated as a pharmaceutical composition that contains an effective dosage amount of CCI-779 polymorph Form II in combination with one or more pharmaceutically acceptable carrier(s).

In still another embodiment, the pharmaceutical composition comprises an effective dosage of a CCI-779 composition that comprises at least a certain percentage of CCI-779 polymorph Form II (based on the total amount of CCI-779 present in the composition, i.e., the total amount of CCI-779 forms being 100%). In other words, at least a certain percentage of CCI-779 present within the pharmaceutical composition exists as CCI-779 polymorph Form II, with the remainder of CCI-779 being in a different form, including (but not limited to) CCI-779, CCI-779 polymorph Form I, or any other crystalline, polymorphic, solvate or amorphous form(s). The compositions described herein containing CCI-779 polymorph Form II can be formulated in any form suitable for the desired route of delivery using a pharmaceutically effective amount of CCI-779 polymorph Form II. For example, the compositions of the invention can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral.

The oral dosage tablet composition of this invention can also be used to make oral dosage tablets containing derivatives of CCI-779 polymorph Form II, including, but not limited to, esters, carbamates, sulfates, ethers, oximes, carbonates, the like which are known to those of skill in the art.

A pharmaceutically effective amount of CCI-779 polymorph Form II can vary depending on the specific compound (s), mode of delivery, severity of the condition being treated, and any other active ingredients used in the composition. The dosing regimen can also be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. However, daily dosages can be lowered or raised based on the periodic delivery.

CCI-779 polymorph Form II can be combined with one or more pharmaceutically acceptable carriers or excipients including, without limitation, solid and liquid carriers that are compatible with the compositions of the present invention. Such carriers include adjuvants, syrups, elixirs, diluents, binders, surfactants, water soluble polymers, lubricants, surfactants, granulating agents, disintegrating agents, emollients, metal chelators, pH adjustors, surfactants, fillers, disintegrants, suspending and stabilizing agents, and combinations thereof, among others. In one embodiment, CCI-779 polymorph Form II is combined with metal chelators, pH adjustors, surfactants, fillers, disintegrants, lubricants, and binders.

Adjuvants can include, without limitation, flavoring agents, coloring agents, preservatives, and supplemental antioxidants, which can include vitamin E, citric acid, ascorbic acid, butylated hydroxytoluene (BHT), butylated hydroxyanisole (BHA), d,l-α-tocopherol, monothioglycerol, and propyl gallate. Typical concentrations of the antioxidants utilized in the oral formulations used in this invention may be used in concentrations ranging from 0.0005 to 0.5% w/v.

Lubricants can include magnesium stearate, light anhydrous silicic acid, talc, stearic acid, sodium lauryl sulfate, and sodium stearyl furamate, among others. In one embodiment, the lubricant is magnesium stearate, stearic acid, or sodium stearyl furamate. In another embodiment, the lubricant is magnesium stearate.

Granulating agents can include, without limitation, silicon dioxide, microcrystalline cellulose, starch, calcium carbonate, pectin, and crospovidone, polyplasdone, among others.

Binders, fillers, and disintegrants can include starch, mannitol, calcium phosphate, sugars such as sucrose, kaolin, lactose, and dextrose, croscarmellose sodium, magnesium stearate, gum acacia and arabic, cholesterol, tragacanth, stearic acid, gelatin, casein, lecithin (phosphatides), carboxymethylcellulose, carboxymethylcellulose calcium, carboxymethylcellulose sodium, methylcellulose, hydroxyethylcellulose, hydroxymethylcellulose, hydroxypropylcellulose, hydroxypropylmethylcellulose phthalate, noncrystalline cellulose, microcrystalline cellulose, cetostearyl alcohol, cetyl alcohol, cetyl esters wax, dextrates, dextrin, glyceryl monooleate, glyceryl monostearate, glyceryl palmitostearate, polyoxyethylene alkyl ethers, polyethylene glycols, polyoxyethylene castor oil derivatives, polyoxyethylene stearates, polyvinyl alcohol, substituted sodium bicarbonate, calcium citrate, sodium starch glycolate, pregelatinized starch, crospovidone, polypropylpyrrolidone, polyvinylpyrrolidone (povidone, PVP), cholesterol, stearic acid, gelatin, casein, lecithin (phosphatides), and the like may also be incorporated into the oral formulation.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants can include nonionic and anionic agents including polysorbates such as polysorbate 20 and 80, sorbitan esters, poloxamers such as poloxamer 188, sodium lauryl sulfate, sodium dodecyl sulfate, benzalkonium chloride, calcium stearate, cetostearyl alcohol, cetomacrogol emulsifying wax, colloidal silicon dioxide, phosphates, magnesium aluminum silicate, triethanolamine, or salts of bile acids (taurocholate, glycocholate, cholate, deoxycholate, etc.) that may be combined with lecithin. The surfactants can also include ethoxylated vegetable oils, such as Cremophor EL or pegylated castor oil (e.g., such as PEG-35 castor oil which is sold, e.g., under the name Cremophor EL, BASF), vitamin E tocopherol propylene glycol succinate (Vitamin E TGPS), polyoxyethylene-polyoxypropylene block copolymers, and poloxamers. It is expected that the surfactant can contain 0.5 to 100% w/v of the composition, 0.5 to 10% w/v, 5 to 80% w/v, 10 to 75% w/v, 15 to 60% w/v, and preferably, at least 5% w/v or at least 10% w/v, of the composition.

Metal chelators can include physiologically acceptable chelating agents including edetic acid, malic acid, fumaric acid, ethylene diamine tetra acetic acid (EDTA), or amino acids such as glycine that are capable of enhancing the stability of CCI-779 polymorph Form II. In one embodiment, the metal chelator is edetic acid.

pH adjusters can also be utilized to adjust the pH of a solution containing CCI-779 to about 4 to about 6. In one embodiment, the pH of a solution containing CCI-779 is adjusted to a pH of about 4.6. pH adjustors can include physiologically acceptable agents including citric acid, ascorbic acid, fumaric acid, malic acid, or dilute hydrochloric acid, and salts thereof. In one embodiment, the pH adjuster is citric acid.

Water-soluble polymers include, but are not limited to, polyvinylpyrrolidone (PVP), hydroxypropylmethylcellulose (HPMC), polyethylene glycol (PEG), and cyclodextrin or mixtures thereof. It is preferred that the water-soluble polymer is PVP, and having a molecular weight of between 2.5 and 60 kilodaltons. Any given oral formulation useful in the invention may contain multiple ingredients of each class of component. For example, an oral formulation containing an antioxidant may contain one or more antioxidants as the antioxidant component.

Suspending or stabilizing agents can include, but are not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar.

Diluents can include water, ethanol, polyethylene glycol 300, polyethylene 400, polyethylene 600, polyethylene 1000, or blends containing one or more of these polyethylene glycols, propylene glycol and other pharmaceutically acceptable cosolvents or agents to adjust solution osmolarity such as sodium chloride, lactose, mannitol or other parenterally acceptable sugars, polyols and electrolytes.

In one embodiment, compositions containing CCI-779 polymorph Form II are delivered orally by tablet, caplet or capsule, microcapsules, dispersible powder, granule, suspension, syrup, elixir, and aerosol. Desirably, when compositions containing CCI-779 polymorph Form II are delivered orally, delivery is by tablets and hard- or liquid-filled capsules.

Non-alcoholic solvents can include dimethylacetamide, dimethylsulfoxide acetonitrile, or mixtures thereof, among others.

Alcoholic solvents can include one or more alcohols as the alcoholic solvent component of the formulation.

Particularly suitable oral formulations for CCI-779 polymorph Form II include the same formulations utilized with CCI-779 and described in US Patent Publication No. 20040077677 and International Patent Publication No. WO 2004/026280, which are hereby incorporated by reference. Such oral formulations contain a granulation prepared using a wet granulation process. The granulation can contain CCI-779 polymorph Form II, a water-soluble polymer, a pH modifying agent, a surfactant, and an antioxidant. In one embodiment, the formulation contains from 0.1 to 30%, from 0.5 to 25%, from 1 to 20%, from 5 to 15%, or from 7 to 12% (wt/wt) CCI-779 polymorph Form II; from 0.5 to 50%, from 1 to 40%, from 5 to 35%, from 10 to 25%, or from 15 to 20% (wt/wt) water soluble polymer; from 0.5 to 10%, 1 to 8%, or 3 to 5% (wt/wt) surfactant; and from 0.001 to 1%, 0.01 to 1%, or 0.1 to 0.5% (wt/wt) antioxidant. However, other embodiments may contain more, or less, of these components.

In another embodiment, the compositions containing CCI-779 polymorph Form II can be delivered intravenously, intramuscularly, subcutaneously, parenterally and intraperitoneally in the form of sterile injectable solutions, suspensions, dispersions, and powders which are fluid to the extent that easy syringe ability exits. Such injectable compositions are sterile and stable under conditions of manufacture and storage, and free of the contaminating action of microorganisms such as bacteria and fungi. Under ordinary conditions of storage and use, these preparations contain a preservative to prevent the growth of microorganisms.

A parenteral formulation useful in the invention can be prepared as a single solution, or preferably can be prepared as a cosolvent concentrate containing CCI-779 polymorph Form II, an alcoholic solvent, and an antioxidant, which is subsequently combined with a diluent that contains a diluent solvent and suitable surfactant.

When prepared as a single solution or dispersion, CCI-779 polymorph Form II is combined with a diluent. In one embodiment, CCI-779 polymorph Form II is combined with water, optionally mixed with a surfactant such as hydroxypropylcellulose. Dispersions can be prepared in glycerol, liquid polyethylene glycols and mixtures thereof in oils.

Particularly suitable injectable formulations for CCI-779 polymorph Form II include those injectable formulations utilized for CCI-779 in International Patent Publication No. WO 2004/011000 and US Patent Application Publication No. US 2004-0167152-A1, which are hereby incorporated by reference. Any given formulation useful in this invention may contain multiple ingredients of each class of component. In one embodiment, a parenterally acceptable solvent can include a non-alcoholic solvent, an alcoholic solvent, or mixtures thereof. Examples of solvents useful in the formulations invention include, without limitation, ethanol, propylene glycol, polyethylene glycol 300, polyethylene glycol 400, polyethylene glycol 600, polyethylene glycol 1000, or mixtures thereof. These solvents are particularly desirable because degradation via oxidation and lactone cleavage occurs to a lower extent for these cosolvents. Further, ethanol and propylene glycol can be combined to produce a less flammable product, but larger amounts of ethanol in the mixture generally result in better chemical stability. A concentration of 30 to 100% v/v of ethanol in the mixture is preferred.

The stability of CCI-779 polymorph Form II in the parenterally acceptable alcoholic cosolvents can be enhanced by addition of an antioxidant to the formulation. Generally, the parenteral formulations useful in this embodiment of the invention will contain an antioxidant component(s) in a concentration ranging from 0.001 to 1% w/v, or 0.01 to 0.5% w/v, of the cosolvent concentrate, although lower or higher concentrations may be desired. Of the antioxidants, d,l-α-tocopherol is particularly desirable and is used at a concentration of 0.01 to 0.1% w/v with a preferred concentration of 0.075% w/v of the cosolvent concentrate.

Advantageously, in certain embodiments of the parenteral formulations useful in the invention, precipitation of CCI-779 polymorph Form II upon dilution with aqueous infusion solutions or blood is prevented through the use of a surfactant contained in the diluent solution. One particularly desirable surfactant is polysorbate 20 or polysorbate 80, as noted below. However, one of skill in the art may readily select other suitable surfactants.

Prior to use, the cosolvent concentrate is mixed with a diluent comprising a diluent solvent, and a surfactant. When CCI-779 polymorph Form II is prepared as a cosolvent concentrate according to this invention, the concentrate can contain concentrations of CCI-779 polymorph Form II from 0.05 mg/mL, from 2.5 mg/mL, from 5 mg/mL, from 10 mg/mL or from 25 mg/mL up to approximately 50 mg/mL. The concentrate can be mixed with the diluent up to approximately 1 part concentrate to 1 part diluent, to give parenteral formulations having concentrations of CCI-779 polymorph Form II from 1 mg/mL, from 5 mg/mL, from 10 mg/mL, from 20 mg/mL, up to approximately 25 mg/mL. For example the concentration of CCI-779 polymorph Form II in the parenteral formulation may be from about 2.5 to 10 mg/mL. This invention also covers the use of formulations having lesser concentrations of CCI-779 polymorph Form II in the cosolvent concentrate, and formulations in which one part of the concentrate is mixed with greater than 1 part of the diluent, e.g., concentrate:diluent in a ratio of about 1:1.5, 1:2, 1:3, 1:4, 1:5, or 1:9 v/v and so on, to CCI-779 polymorph Form II parenteral formulations having a CCI-779 polymorph Form II concentration down to the lowest levels of detection.

For the purposes of this disclosure, transdermal administrations are understood to include all administrations across the surface of the body and the inner linings of bodily passages including epithelial and mucosal tissues. Such administrations may be carried out using CCI-779 polymorph Form II, or pharmaceutically acceptable salts thereof, in lotions, creams, foams, patches, suspensions, solutions, and suppositories (rectal and vaginal).

Transdermal administration may be accomplished through the use of a transdermal patch containing CCI-779 polymorph Form II and a carrier that is inert to CCI-779 polymorph Form II, is non-toxic to the skin, and allows delivery of the agent for systemic absorption into the blood stream via the skin. The carrier may take any number of forms such as creams and ointments, pastes, gels, and occlusive devices. The creams and ointments may be viscous liquids or semisolid emulsions of either the oil-in-water or water-in-oil type. Pastes comprised of absorptive powders dispersed in petroleum or hydrophilic petroleum containing CCI-779 polymorph Form II may also be suitable. A variety of occlusive devices may be used to release CCI-779 polymorph Form II into the blood stream such as a semi-permeable membrane covering a reservoir containing CCI-779 polymorph Form II with or without a carrier, or a matrix containing CCI-779 polymorph Form II. Other occlusive devices are known in the literature.

In a further embodiment, compositions containing CCI-779 polymorph Form II can be delivered rectally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

In another embodiment, compositions containing CCI-779 polymorph Form II can be delivered vaginally in the form of a conventional suppository, cream, gel, ring, or coated intrauterine device (IUD).

In yet another embodiment, compositions containing CCI-779 polymorph Form II can be delivered intranasally or intrabronchially in the form of an aerosol.

It is also contemplated that compositions of this invention containing CCI-779 polymorph Form II can be co-administered with one or more other agents including anti-rejection chemotherapeutic agents.

The dosage requirements of CCI-779 polymorph Form II can vary depending on the severity of the symptoms presented, the particular subject being treated, and the route of administration. One of skill in the art would readily be able to determine the amount of CCI-779 polymorph Form II required. In one embodiment, about 2 to about 100 mg/day of CCI-779 polymorph Form II is administered. In other embodiments, CCI-779 polymorph Form II is administered at 5 mg/day to 75 mg/day, 10 mg/day to 50 mg/day, 15 mg/day to 35 mg/day, or about 20 mg/day to 25 mg/day.

Treatment can be initiated with dosages of CCI-779 polymorph Form II smaller than those required to produce a desired effect and generally less than the optimum dose of CCI-779 polymorph Form II. Thereafter, the dosage can be increased until the optimum effect under the circumstances is reached. Precise dosages will be determined by the administering physician based on experience with the individual subject being treated. In general, the compositions of this invention are most desirably administered at a concentration that will generally afford effective results without causing any harmful or deleterious side effects.

IV. Methods of Preparing Administrable Compositions Containing CCI-779 Polymorph Form II In one aspect, the present invention includes methods of preparing a pharmaceutical composition containing CCI-779 polymorph Form II. The composition can be administered to a mammalian subject by several different routes as noted above and is desirably administered orally in solid or liquid form.

Oral formulations containing CCI-779 polymorph Form II can contain any conventionally used oral forms, including tablets, capsules, buccal forms, troches, lozenges and oral liquids, suspensions or solutions. Such oral formulations containing CCI-779 polymorph Form II can be formed by blending CCI-779 polymorph Form II with one or more of the components described above. In one embodiment, the components of the composition are dry or wet blended. In another embodiment, the components are dry granulated. In a further embodiment, the components are suspended or dissolved in a liquid and added to a form suitable for administration to a mammalian subject. Oral formulations can also include standard delay or time-release formulations to alter the absorption of CCI-779 polymorph Form II. The oral formulation may also consist of administering CCI-779 polymorph Form II in water or a fruit juice, containing appropriate solubilizers or emulsifiers as needed.

Capsules may contain mixtures of CCI-779 polymorph Form II with fillers and/or diluents such as the pharmaceutically acceptable starches (e.g corn, potato or tapioca starch), sugars, artificial sweetening agents, powdered celluloses, such as crystalline and microcrystalline celluloses, flours, gelatins, gums, etc, described above.

Useful tablet formulations may be made by conventional compression, wet granulation or dry granulation methods and utilize pharmaceutically acceptable diluents, binding agents, lubricants, disintegrants, surface modifying agents (including surfactants). It is preferred that the wet granulation be performed with a hydroalcoholic solvent system comprising water and an alcohol, with ethanol being the preferred alcoholic component.

Liquid forms containing CCI-779 polymorph Form II can be formed by dissolving or suspending CCI-779 polymorph Form II in a liquid suitable for administration to a mammalian subject.

In one embodiment, methods of preparing a pharmaceutical composition containing CCI-779 polymorph Form II include combining CCI-779 polymorph Form II, a metal chelator, a pH adjuster, a surfactant, a filler, a binder, a disintegrant, and a lubricant.

In another embodiment, methods of preparing a pharmaceutical composition containing CCI-779 polymorph Form II include combining CCI-779 polymorph Form II, a metal chelator, a pH adjuster, a surfactant, at least one filler, a binder, a disintegrant, and a lubricant.

The present invention also provides kits or packages of pharmaceutical compositions designed for use in the present invention. Kits of the present invention can include CCI-779 polymorph Form II and a carrier suitable for administration to a mammalian subject as discussed above. The invention therefore includes a product containing CCI-779 polymorph Form II for use in treating a mammal. The invention also includes a pharmaceutical pack containing a course of treatment of a neoplasm for one individual mammal, wherein the pack contains CCI-779 polymorph Form II in unit dosage form.

Thus, CCI-779 polymorph Form II of the invention can be formulated as a pharmaceutical composition and, optionally, assembled in the form of a kit, for use in treatment of a mammal.

V. Methods of Using CCI-779 Polymorph Form II

CCI-779 polymorph Form II can be utilized in the treatment or prevention of a variety of conditions known to those of skill in the art that CCI-779 is known to treat or prevent. CCI-779 polymorph Form II can therefore possess immunosuppressive, antirejection, antifungal, anti-inflammatory, antitumor, and antiproliferative activities.

Specifically, CCI-779 polymorph Form II alone or in a composition or kit prepared as noted above can be used as an antineoplastic agent, and in particular, in treatment of solid tumors, including sarcomas and carcinomas; and more particularly against astrocytomas, prostate cancer, breast cancer, colon cancer, small cell lung cancer, and ovarian cancer; and adult T-cell leukemia/lymphoma. CCI-779 polymorph Form II containing compositions and kits are also useful treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus including systemic lupus erythematosus, rheumatoid arthritis, diabetes mellitus, myasthenia gravis, and multiple sclerosis; and diseases of inflammation such as psoriasis, dermatitis, eczema, seborrhea, bowel disorders including inflammatory bowel disease, pulmonary inflammation (including asthma, chronic obstructive pulmonary disease, emphysema, acute respiratory distress syndrome, bronchitis, and the like), cardiac inflammatory disease, and ocular inflammation such as ocular uveitis; anemia; adult T-cell leukemia/lymphoma; fungal infections; malignant carcinomas; hyperproliferative vascular diseases such as restenosis; graft vascular atherosclerosis; and cardiovascular disease, cerebral vascular disease, and peripheral vascular disease, such as coronary artery disease, cereberovascular disease, arteriosclerosis, atherosclerosis, nonatheromatous arteriosclerosis, vascular wall damage from cellular events leading toward immune mediated vascular damage, smooth muscle cell proliferation and intimal thickening following vascular injury, and inhibiting stroke or multiinfarct dementia.

Appropriate dosage regimens can be readily determined based upon the information provided herein.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLE 1

Preparation of Crystalline Form II

A. Method 1

0.032 g of CCI-779 (Form I) was added to a 5 mL glass vial. Acetone (2 ml) was added and the mixture was stirred at 22° C. to obtain a clear solution. The solution was filtered through a 0.45 µm syringe filter and then distilled at 22-30° C. and 100 mm Hg vacuum to obtain a solid foam. t-butyl methyl ether (t-BME, 1 mL) was added to the foam to obtain a solid suspension. The suspension was stirred at 22° C. for 15 hours and then filtered. The resulting solid was washed with t-BME (1 mL) and dried under vacuum at 22° C. to obtain dry crystalline Form II solid (0.025 g).

B. Method 2

0.75 g of CCI-779 (Form I) was added to a 50 mL glass reactor with overhead stirring. Acetone (20 ml) was added and the mixture was stirred at 22° C. to obtain a clear solution. The solution was filtered through a 0.45 µm syringe filter and then distilled at 22-30° C. and 100 mm Hg vacuum to obtain a solid foam. t-butyl methyl ether (t-BME, 30 ml) was added to the foam to obtain a hazy solution. n-heptane (20 ml) was added to the t-BME solution at a rate of 40 mL/hour. A solid precipitate was observed as the n-heptane addition continued. The resulting suspension (the solid precipitate is suspended in the solvent) was stirred at 22° C. for 15 hours and then filtered. The wet solid was washed with n-heptane (5 mL) and dried under vacuum at 22° C. to obtain dry crystalline Form II solid (0.66 g).

Stable Form II can be prepared as described and stored under room temperature and pressure for greater than 3 months without conversion to Form I.

EXAMPLE 2

Characterization of CCCI-779 Polymorph Form II

A. Powder XRD Pattern of Form I and Form II

The powder X-ray diffraction pattern was obtained on a Rigaku Miniflex Diffraction System (Rigaku MSC Inc.) operated essentially according to manufacturers' instructions. The powder samples were deposited on a zero-background polished silicon sample holder. A normal focus copper x-ray tube at 0.45 kW equipped with a Ni Kβ filter scanning at 0.25E/minute from 3.00 to 40.00E 2θ was used as the x-ray source. The data processing was done using Jade 6.0 software.

The results are shown in FIG. 1.

B. X-ray Diffraction Pattern

Figure 2:
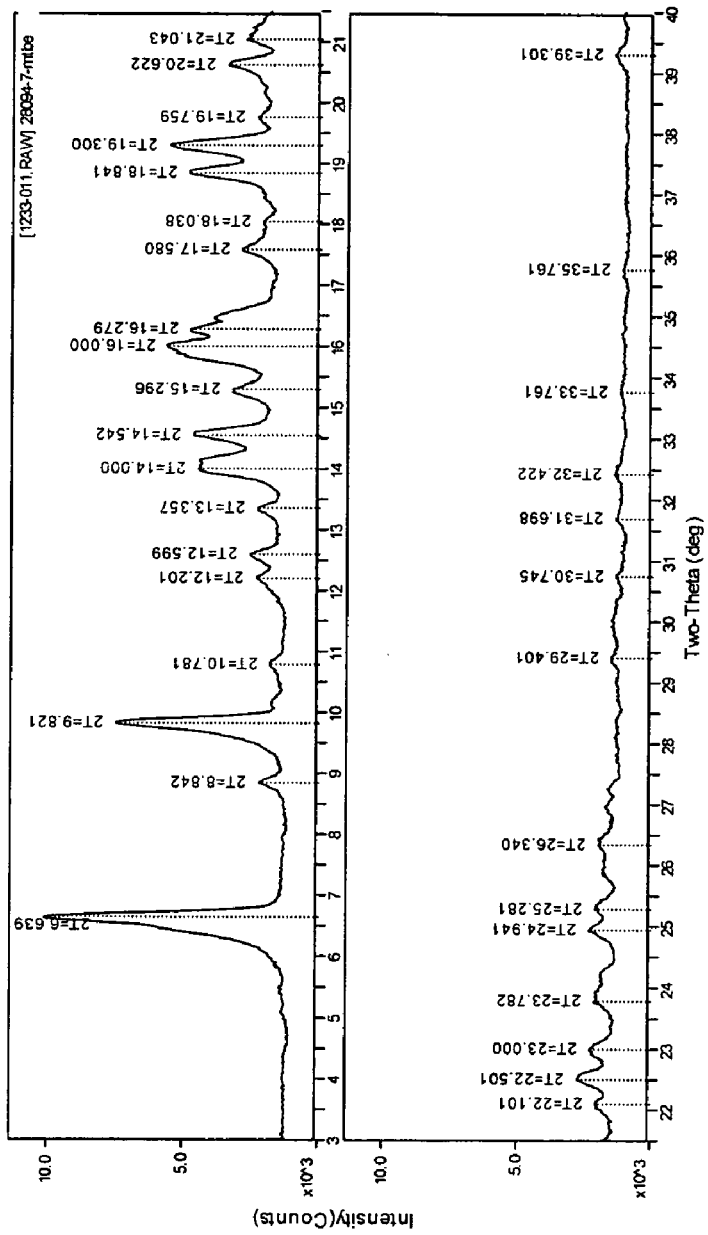
FIG. 2 is a representative XRD pattern for CCI-779 Form II, which displays characteristic lines at 2θ values of 6.6°, 9.8°, 14.0°, 14.1°, 14.5°, and 18.8°.

A representative XRD pattern for Form II displays characteristics lines at 2θ values of 6.6E, 9.8E, 14.0E, 14.1E, 14.5E, and 18.8E. These results are shown in FIG. 2.

C. Differential scanning calorimetry (DSC)

DSC data was collected using a Q1000 DSC (TA instruments), operated according to manufacturer's instructions. The sample was heated from 25-200° C. at a ramp rate of 10° C./min.

Figure 3A:
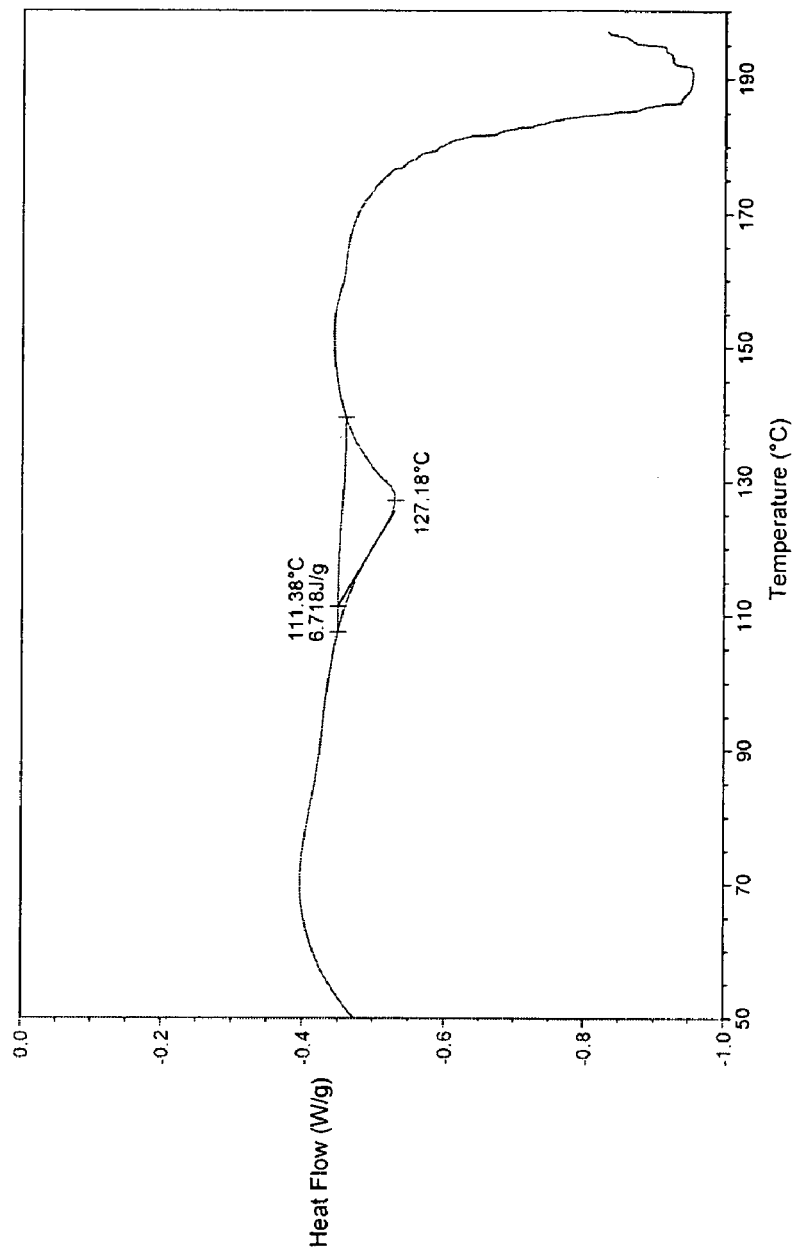
FIG. 3A and FIG. 3B are representative differential scanning calorimetry (DSC) profiles for Form II.
Figure 3B:
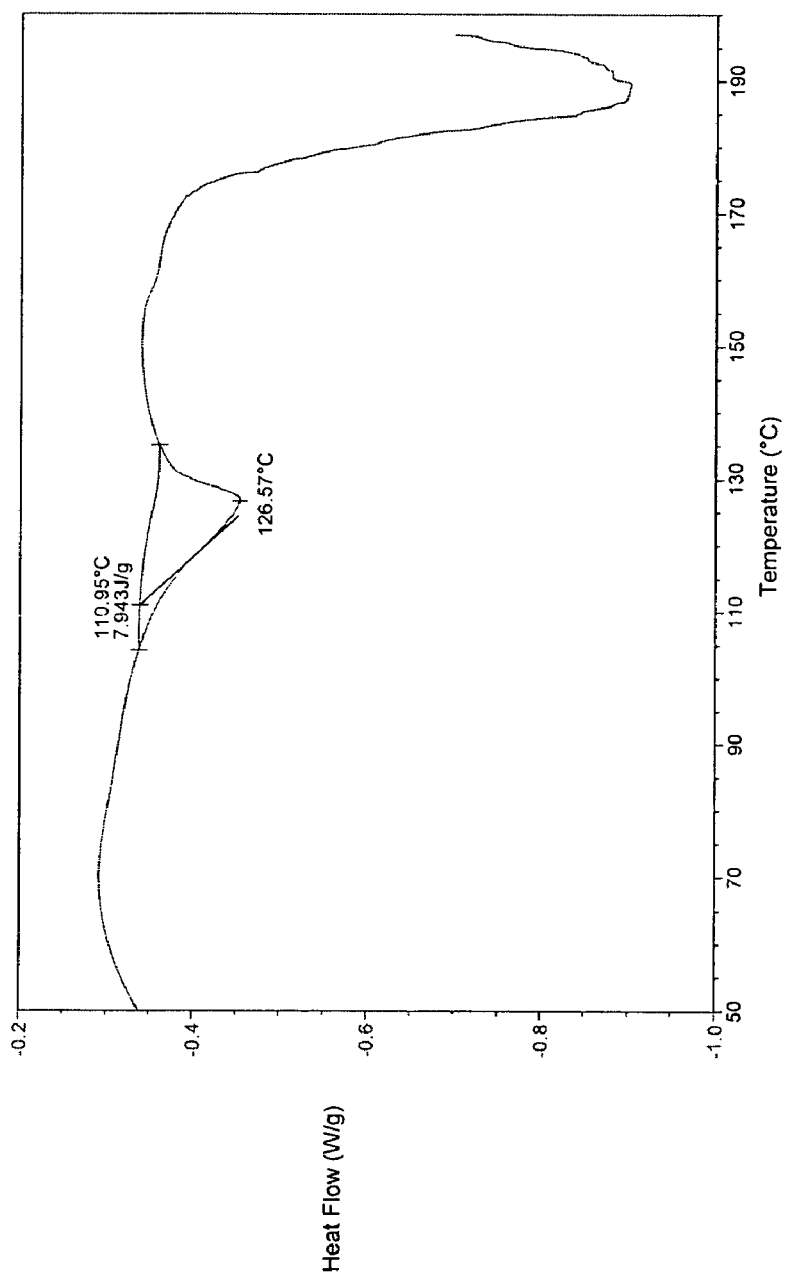

DSC data show a broad melting event with a characteristic onset temperature of 105-115° C., which is easily distinguished from the DSC profile for Form I. These results are shown in FIGS. 3A and 3B.

D. Thermogravimetric Analysis (TGA)

Figure 4:
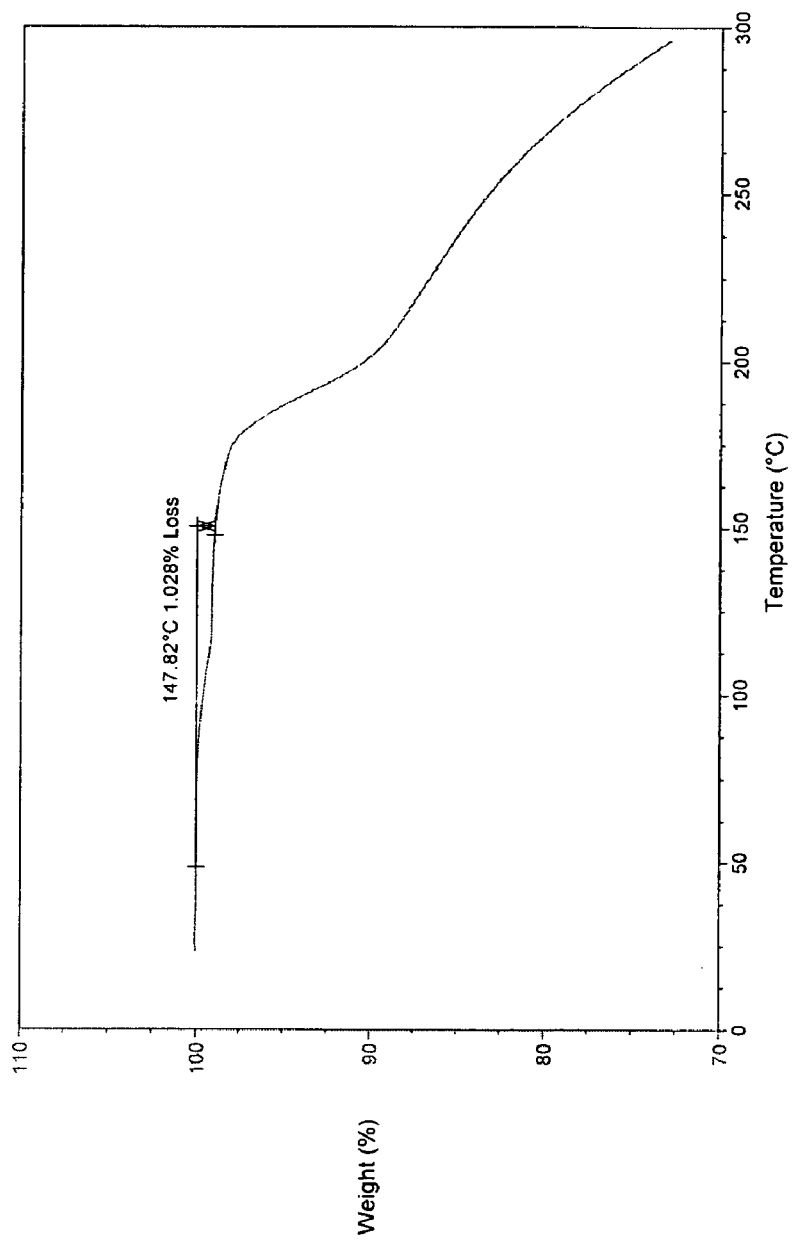
FIG. 4 is a thermographic analysis (TGA) of CCI-779 Form II and shows a gradual weight loss of about 1 wt % on heating from 25-150° C. TGA data was collected using a Q500 thermogravimetric analyzer (TA instruments). Samples were heated under a nitrogen flow from 25-300° C. at 10° C./min.

TGA data was collected using a Q500 thermogravimetric analyzer (TA instruments), operated according to manufacturer's instructions. Samples were heated from 25-300° C. at 10° C./min TGA data shows a gradual weight loss of about 1 wt % on heating from 25-150° C. These results are shown in FIG. 4.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

The invention claimed is:

1. A CCI-779 polymorph having an X-ray diffraction peak pattern lacking peaks at 2θ values of 7.6, 9.5, 11.4, 15.0, 16.8, 18.2, 18.5, and 21.2, and characterized by
    a X-ray diffraction peak pattern comprising peaks at 2θ of about 6.6, 9.8, 14.0, 14.1, 14.5, and 18.8;
    a differential scanning calorimetry thermogram having an endotherm with an onset temperature of about 110° C.;
    and a thermogravimetric analysis of less than 1 wt % weight loss on heating from 25° C. to 150° C.

2. An isolated CCI-779 polymorph Form II obtainable by precipitating said CCI-779 polymorph Form II from a suspension comprising amorphous CCI-779 and t-butyl methyl ether.

3. A process for preparing CCI-779 polymorph Form II, comprising the steps of:
    (a) dissolving CCI-779 in an initial solvent comprising acetone;
    (b) removing said initial solvent in step (a) to form a solid foam;
    (c) mixing the solid foam with t-butyl methyl ether (t-BME) to form a suspension and stirring to afford CCI-779 polymorph Form II; and
    (d) collecting said CCI-779 polymorph Form II.

4. The process according to claim 3, further comprising the step of washing the suspension with t-BME and drying under vacuum to obtain dry crystalline Form II solid.

5. The process according to claim 3, further comprising the step of mixing n-heptane to the mixture of solid foam with t-BME to form a solid suspension.

6. The process according to claim 5, further comprising the step of collecting the solid, washing said solid with n-heptane, and drying under vacuum to obtain dry crystalline Form II solid.

7. A solid pharmaceutical composition comprising CCI-779 polymorph according to claim 1 and a pharmaceutically acceptable carrier.

8. A kit comprising a solid CCI-779 polymorph according to claim 1 and a carrier suitable for administration to a mammalian subject.

9. A method of preparing a solid pharmaceutical composition comprising a CCI-779 according to claim 1, comprising combining one of more of:
    (i) CCI-779 polymorph form II;
    (ii) a metal chelator;
    (iii) a pH adjuster;
    (iv) a surfactant;
    (v) at least one filler;
    (vi) a binder;
    (vii) a disintegrant; and
    (viii) a lubricant.

10. The method according to claim 3, further comprising filtering the stirred suspension to afford a solid and washing the solid with t-BME prior to collecting polymorph form II.

11. The method according to claim 3, wherein the stirring is for about 15hours.

* * * * *